US006594839B1

(12) United States Patent
Papay

(10) Patent No.: US 6,594,839 B1
(45) Date of Patent: Jul. 22, 2003

(54) SURGICAL HEADREST

(75) Inventor: Francis A. Papay, Westlake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/958,240

(22) PCT Filed: May 1, 2000

(86) PCT No.: PCT/US00/11812

§ 371 (c)(1),
(2), (4) Date: Apr. 1, 2002

(87) PCT Pub. No.: WO00/66059

PCT Pub. Date: Nov. 9, 2000

Related U.S. Application Data

(60) Provisional application No. 60/131,808, filed on May 30, 1999.

(51) Int. Cl.7 .......................... A61G 13/12; A61G 13/10
(52) U.S. Cl. .................... 5/637; 5/622; 5/640; 297/405; 297/408
(58) Field of Search ........................... 5/637, 622, 640; 297/405, 408; 606/130

(56) References Cited

U.S. PATENT DOCUMENTS

| 2,966,383 A | 12/1960 | Boetcker et al. |
| 4,064,401 A | 12/1977 | Marden |
| 4,545,572 A | 10/1985 | Day |
| 5,276,927 A | 1/1994 | Day |

Primary Examiner—Alexander Grosz
(74) Attorney, Agent, or Firm—Tarolli, Sundheim, Covell & Tummino L.L.P.

(57) ABSTRACT

A surgical headrest (10) is provided which includes a base plate (20) and at least two support arms (30). Each of the support arms (30) has a first end (31) rotatably mounted to the base plate (20). Each of the support arms (30) also includes a second end (34) for receiving and supporting the head of a patient. The second end (34) may comprise mounting pads (50) which are rotatably mounted for engagement with the patient during surgery. Alternatively, the second end (34) may comprise skull pins (60) for affixing to the head of a patient. The surgical headrest (10) may further include a positioning device (70) having linkage arms (73, 77) which allow for superior/anterior adjustment of a patient's head.

15 Claims, 7 Drawing Sheets

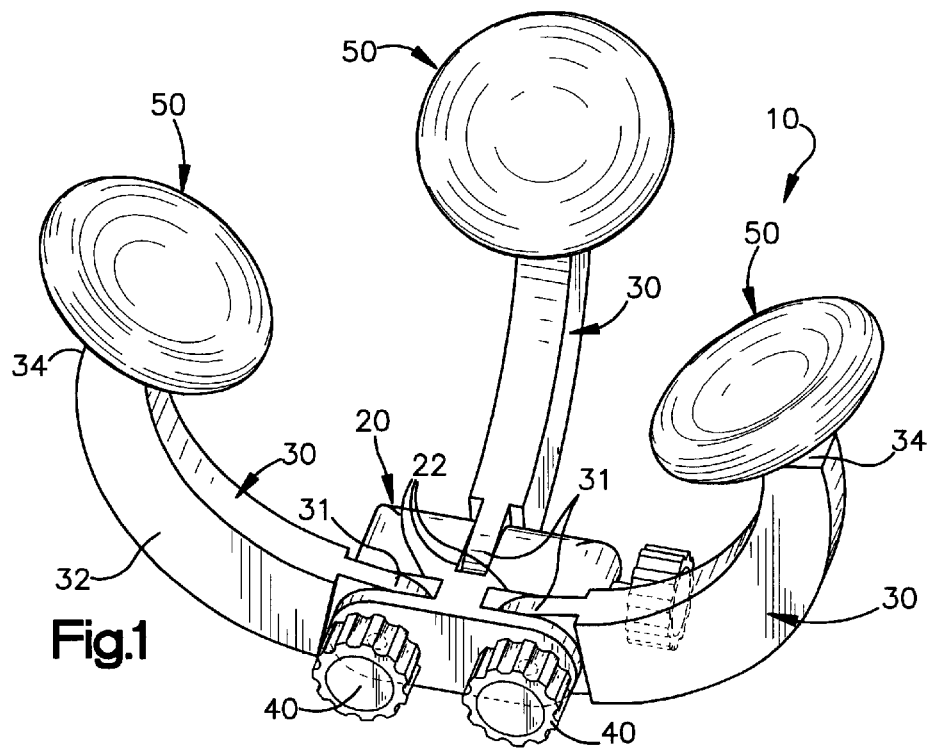
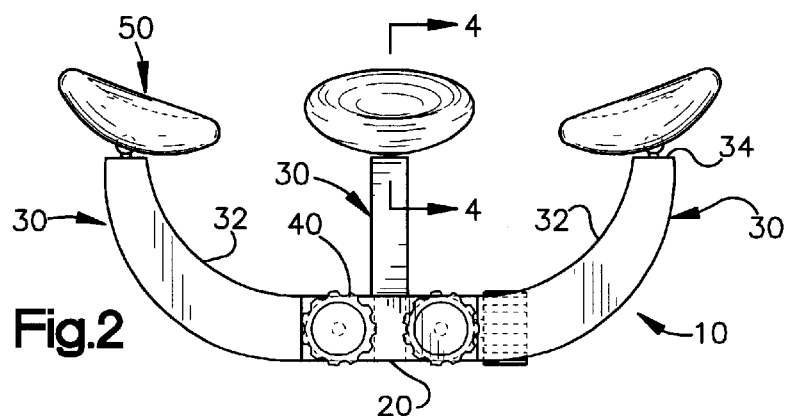
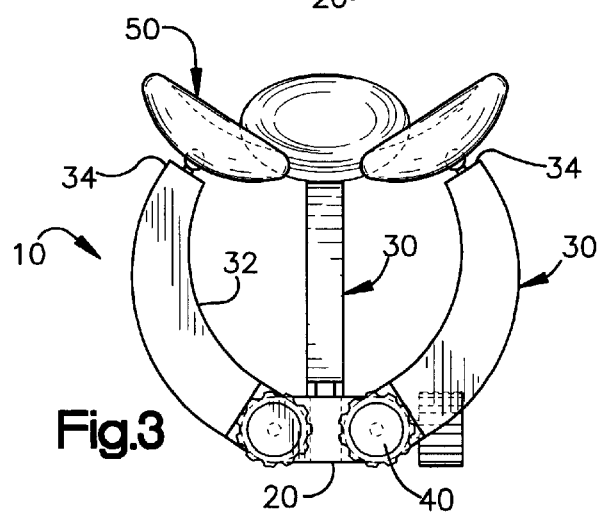

SURGICAL HEADREST

RELATED APPLICATIONS

This application claims the benefit of International Application No. PCT/US00/11812, filed May 1, 2000, which claims priority from U.S. provisional patent application Ser. No. 60/131,808, filed Apr. 30, 1999.

FIELD OF THE INVENTION

The present invention pertains generally to a device for holding the head of a patient undergoing surgery. More particularly, the invention pertains to a device for holding a patient's head in a precise fixed location without positional drift.

BACKGROUND OF THE INVENTION

For patients undergoing cranial neuro-surgery, it is very important that the head of the patient be fixed or locked into a precise position. This is especially important where stereotactic procedures are utilized. It is also important that the physician have full access to the cranial area surrounding the operating field. One problem with prior art surgical headrests is that they inhibit a surgeon's access to the cranial surgical area. Some prior art headrests have stereotactic rings or locating structures which sacrifice surgeon's accessibility for stereotactic precision. Another disadvantage to the prior art headrests is that they do not generally allow for height and angular adjustment of a patient's head with respect to the operating table nor do they provide for prone or supine position of the patient.

It is highly desirable to have a new and improved surgical headrest which allows superior-anterior and lateral adjustment of a patient's head while allowing full orbital access to the region undergoing surgery.

SUMMARY OF THE INVENTION

The invention provides in one aspect a surgical headrest comprising a base plate and at least two support arms each having a first end rotatably mounted to the plate, and a second end having mounting pads rotatably mounted thereon.

The invention provides in another aspect a surgical headrest comprising a base plate and at least two support arms. Each of the arms has a first end rotatably mounted to the plate and a second end having skull screws mounted thereon.

The invention provides in yet another aspect a surgical headrest comprising a base plate and at least two support arms. Each of the arms has a first end rotatably mounted to the plate and a second end for receiving and supporting the head of a patient. The base plate is connected to a positioning device rotatably mounted to an operating table for adjusting the height and angular position of a patient's head with respect to the operating table.

These and other aspects of the invention are herein described in particularized detail with reference to the accompanying figures.

DETAILED DESCRIPTION OF THE FIGURES

In the accompanying figures:

FIG. 1 is a schematic perspective view of a first embodiment of a surgical headrest of the present invention;

FIG. 2 is a schematic front view of the headrest as shown in FIG. 1;

FIG. 3 is a front view of the headrest shown with the arms in the fully retracted position;

Figure 9A:
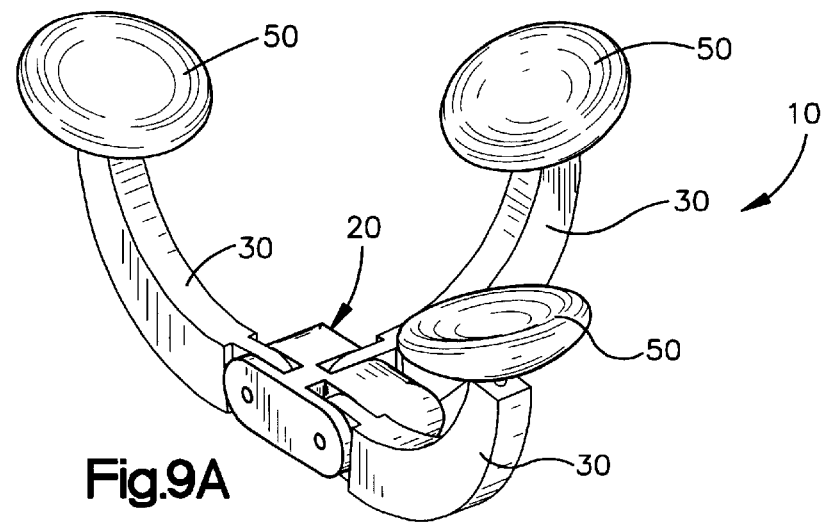
Figure 9B:
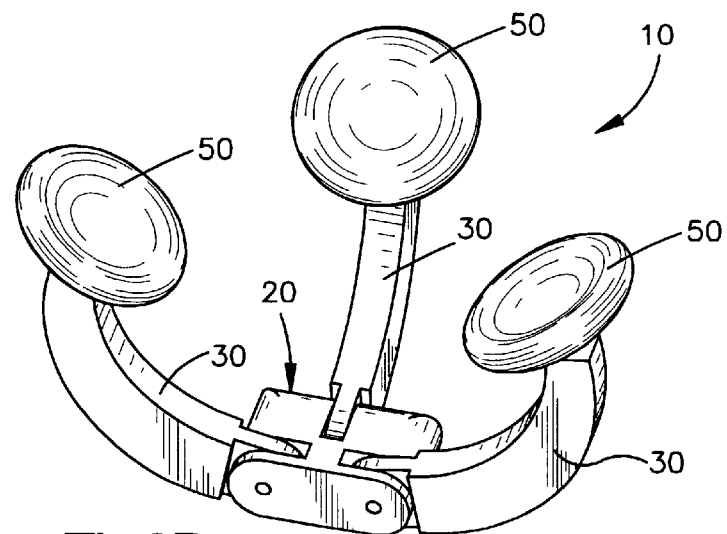
Figure 9C:
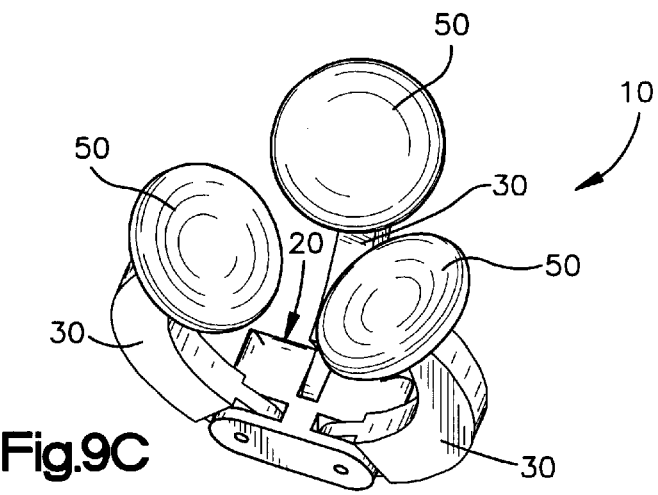

FIGS. 8A–F illustrate the adjustment mechanism illustrated in various positions; and FIGS. 9A–9C illustrate the surgical headrest in various positions.

DETAILED DESCRIPTION OF PREFERRED AND ALTERNATE EMBODIMENTS

Turning to the drawings, and particularly FIGS. 1–3, there is shown a first embodiment of the surgical headrest 10. The headrest 10 comprises a base plate 20 which may be primarily rectangular or square in shape with preferably rounded edges. The base plate 20 further comprises three slots 22 for rotatably mounting two or more arms 30. Holes (not shown) of the first ends 31 of the arms 30 align with threaded holes (not shown) of the slots 22. The first ends 31 of the arms 30 are preferably rounded to facilitate rotation of the arms 30 within the slot 22. Locking screws 40 allow for the arms 30 to be easily adjusted and locked or fixed into a desired position by medical personnel. It is important to note that the surgical headrest 10 allows for the head of the patient to be oriented in virtually any desired position, an advantage not found in the prior art.

Figure 4:
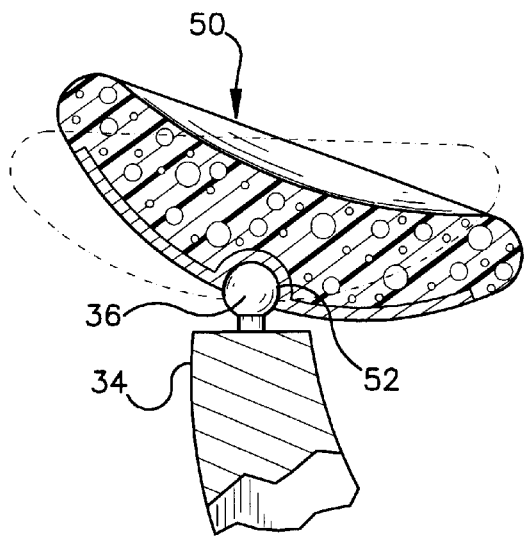
FIG. 4 is a close up view of the pad assembly of the headrest as shown in FIG. 1.
Figure 6:
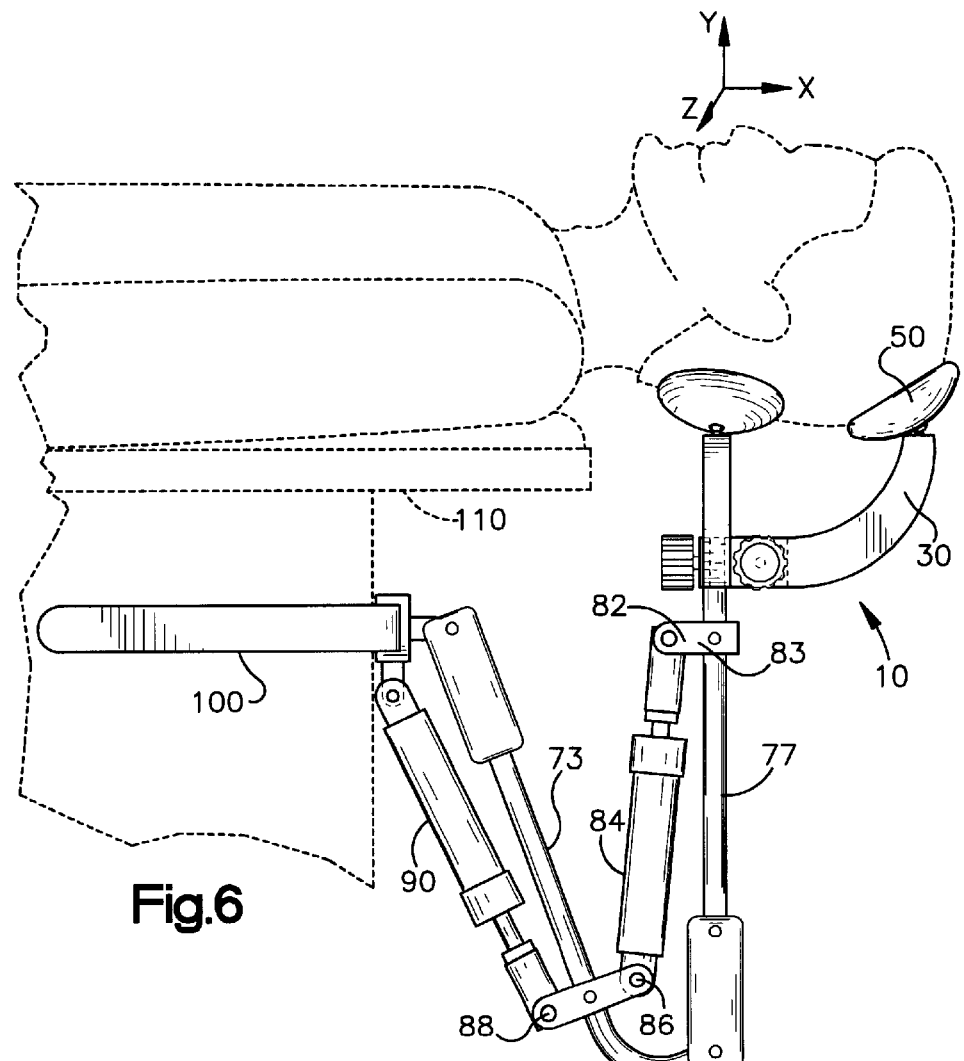
FIG. 6 is a side elevational view of the surgical headrest of FIG. 1 shown in use with the adjustment shown mechanism mounted on a operating table.
Figure 7:
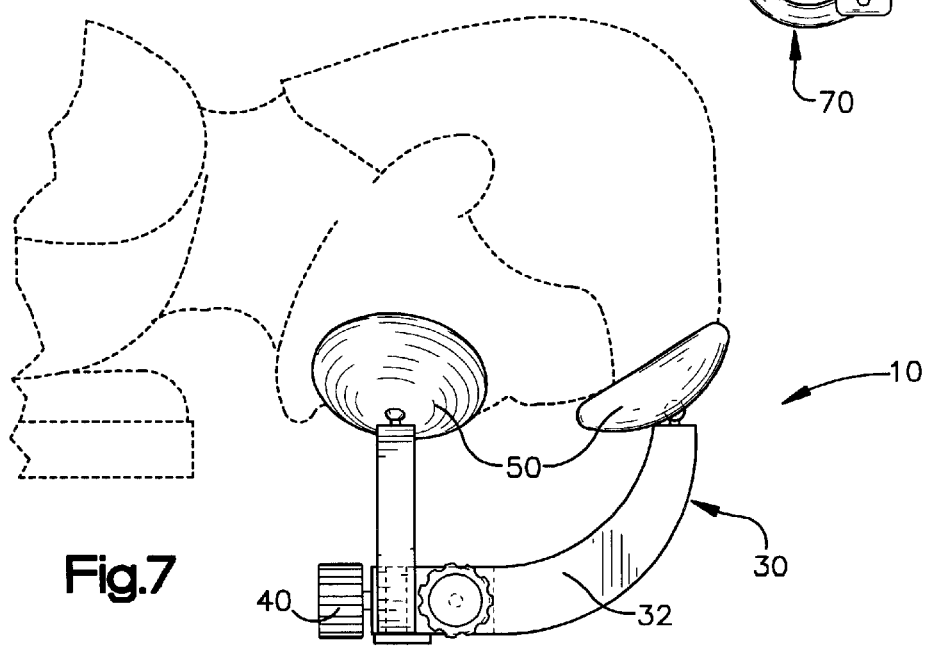
FIG. 7 is a side elevational view of the surgical headrest of FIG. 1 shown with the head of the patient in phantom where the patient is in the prone position.
Figure 8A:
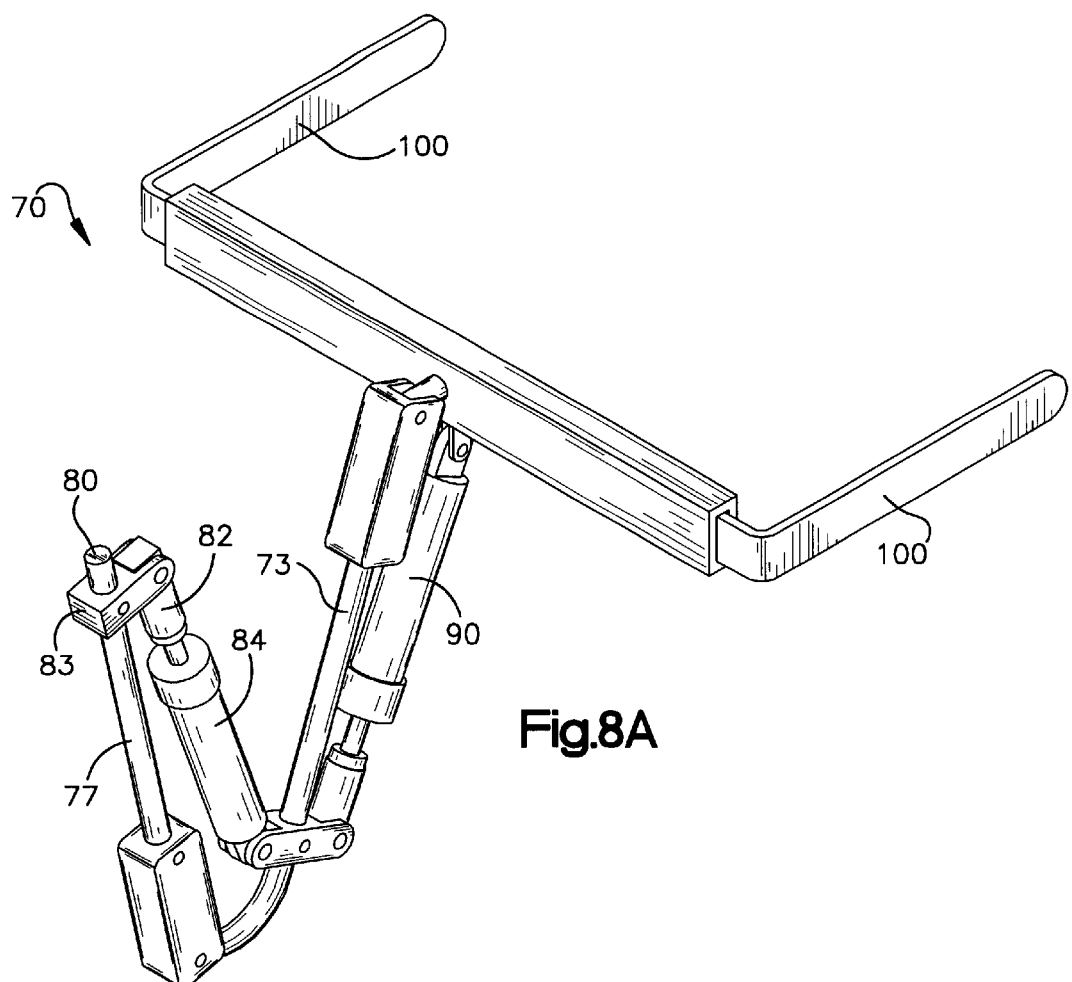
Figure 8B:
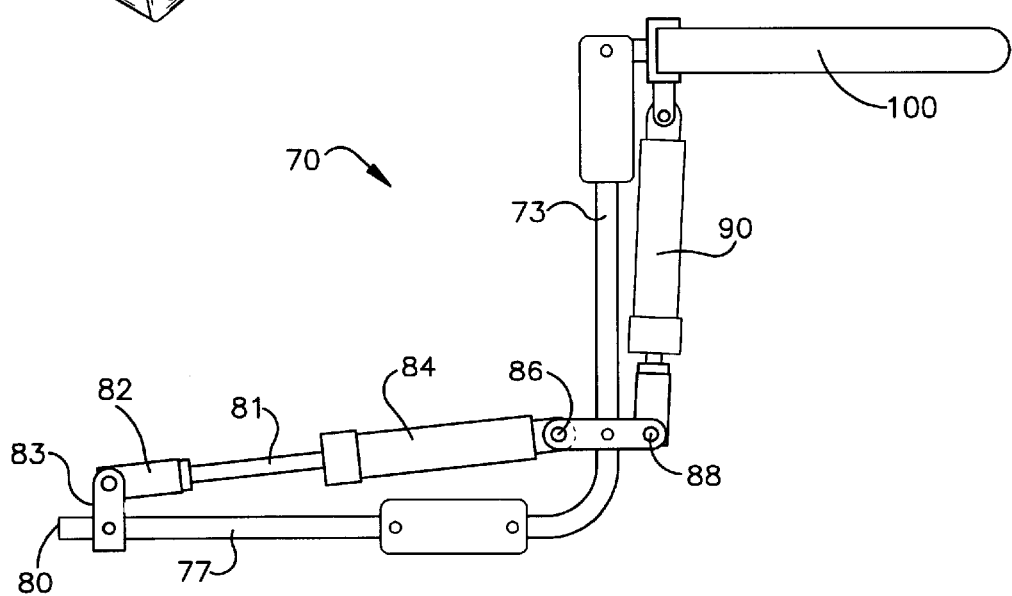
Figure 8C:
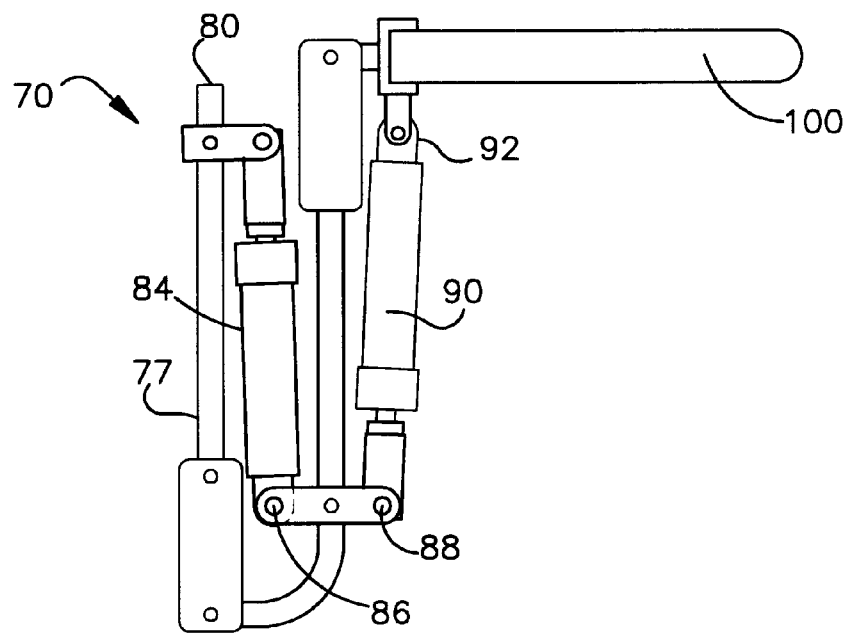
Figure 8D:
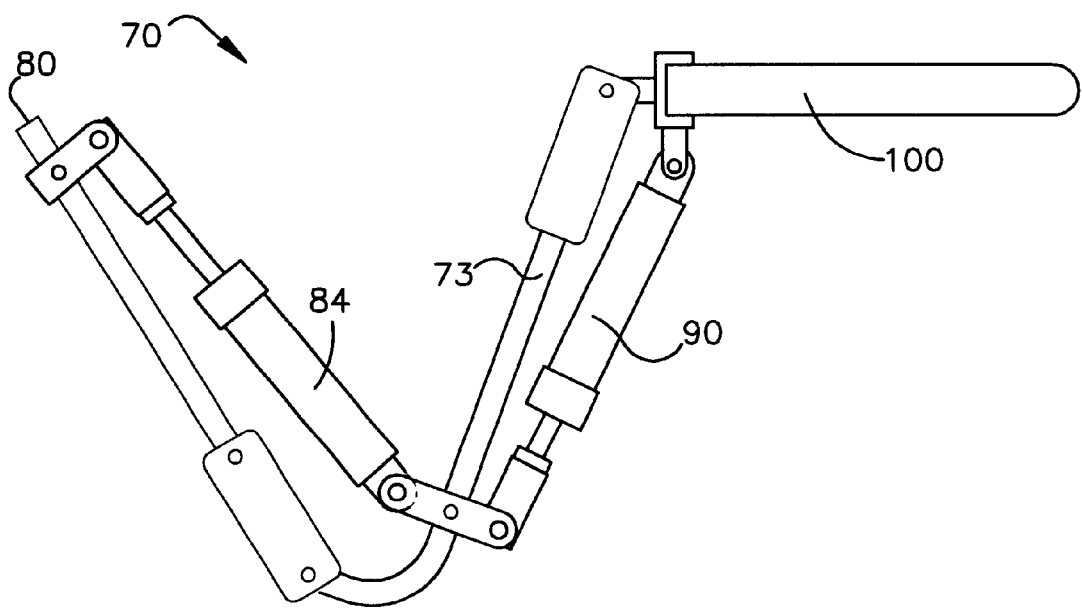
Figure 8E:
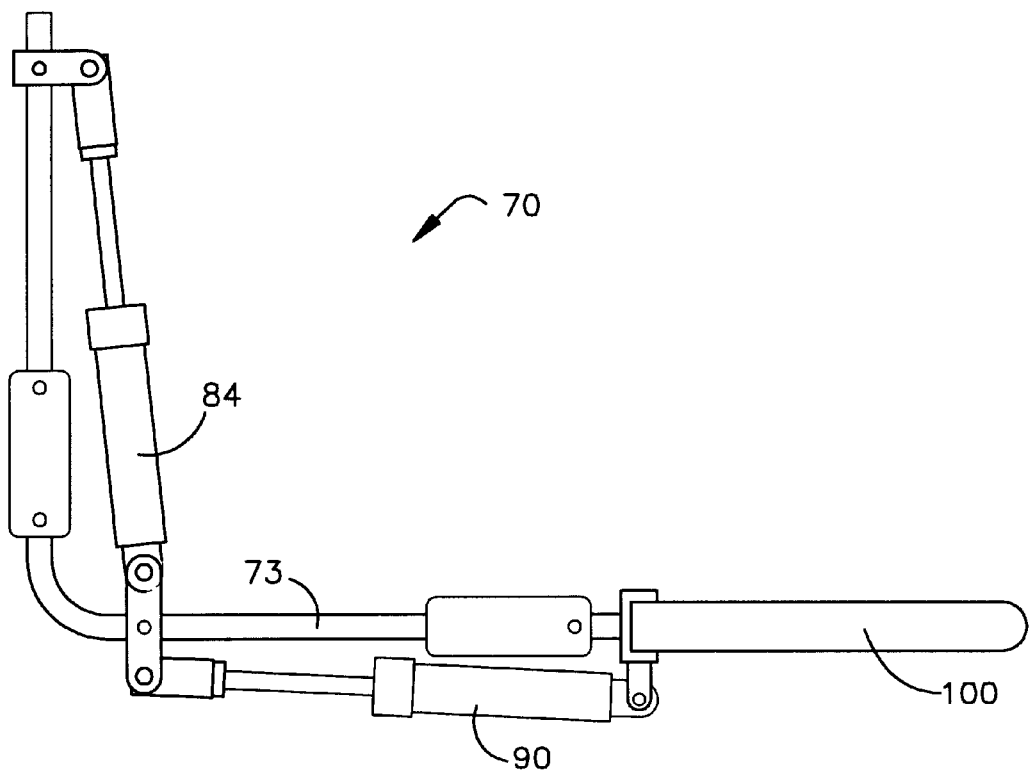
Figure 8F:
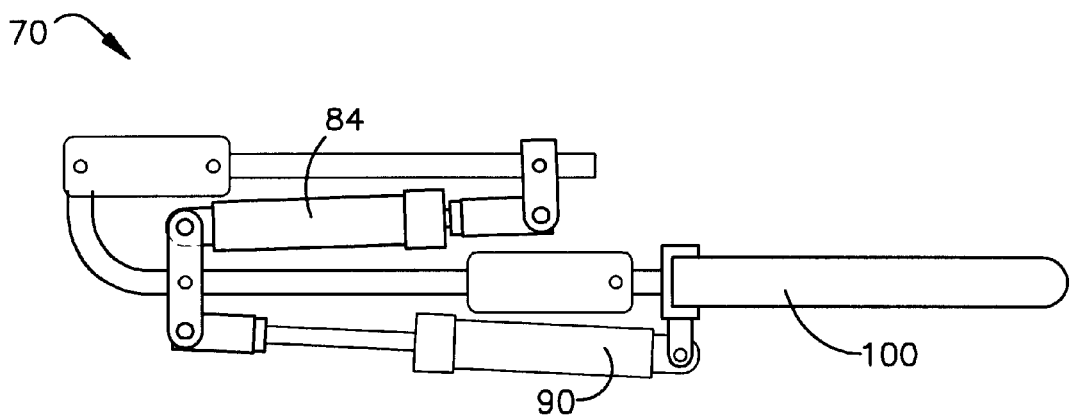

The middle portion 32 of arms 30 are preferably curved upward such that the second end 34 is oriented at approximately a ninety degree angle with respect to the first end 32. As shown in FIG. 4, a ball joint-like structure 36 may be secured to the second end 32 for mounting within a socket 52 of replaceable mounting pads 50. Other attachment structures may also be utilized to attach the mounting pads 50 to the arms 30 which are readily apparent to those skilled in the art. While a fixed or pinned connection may be utilized, it is preferred that the mounting pads be positionable or rotatably mounted. The mounting pads 50 preferably comprise soft compressible foam or rubber material, gel pad or soft plastic or polymeric material. The pads 50 may be readily removable so that they may be replaced with sterile pads. As shown in FIG. 7, the pads 50 may be positioned to engage the cheekbones and upper forehead region of a patient positioned in the prone position. Alternatively, the patient may be positioned on his/her back, such that the backside of the head is supported by the headrest 10 as shown in FIG. 6. The headrest 10 is not limited to these two patient positions, as many other head positions may be feasible e.g., the head of the patient could be rotated laterally and supported by the headrest (not shown).

Figure 5:
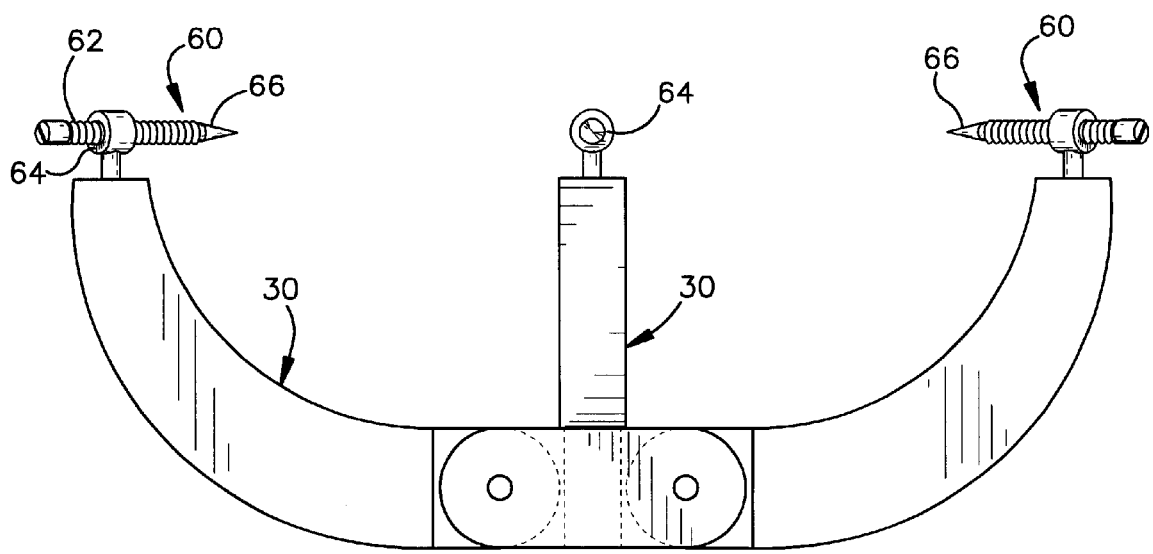
FIG. 5 is an alternative embodiment of the surgical headrest shown with attachment screws.

In an alternate embodiment of the invention as shown in FIG. 5, skull pins 60 are mounted upon the arms 30 of the surgical headrest 10 to allow the precise positioning of a patient's head without the disadvantage of positional drift. This is particularly useful where stereotactic surgery is required. The surgical headrest 10 allows a surgeon virtually unlimited access to the cranial region of the patient's head without the unnecessary interference of the headrest or prior art stereotactic rings or devices. The surgeon may use fiducial markers mounted on the patient or anatomical landmarks. The threaded ends 62 of skull pins 60 are received within support brackets 64. The brackets 64 are fixably mounted upon the flanged end 34 of arms 30. The skull pins 60 when rotated relative to the brackets 64, extend inwardly to engage the patient's skull or retract outwardly to disengage from the patient's skull. The skull pins 60 have pointed tips or ends 66 which penetrate the outer tissue of the patient's head to engage the bone of the skull in order to rigidly and invasively affix the surgical headrest 10 to the patient's skull. The skull pins may also be used in combination with the support pads 50.

The base plate 20 of the surgical headrest 10 may be mounted to the operating table as shown in FIG. 6 by a positioning device 70. The positioning device 70 is further shown in FIGS. 8A–F in various positions. The positioning device 70 comprises a first end 80 for mounting the base plate 20 thereon, and a second end further comprising a forked mounting bracket 100 for securing to an operating table 110. The positioning device 70 further comprises linkage arm 73 which is rotatably or pin connected to the mounting bracket 100. Linkage arm 73 is rotatably connected to linkage arm 77, the end of which is connected to the surgical headrest 10. It is preferred that the linkage arms 73, 77 further comprise means for locking the joints (not shown) into a fixed position once the desired positions have been reached. The linkage arms 73, 77 allow the surgical headrest 10 to be vertically, raised and lowered with respect to the operating table 110 as well as allow the headrest 10 to be rotated about axis Z as illustrated in FIG. 6. Thus, as illustrated in FIG. 6, the positioning device will allow the patient's head to be adjusted in the superior/anterior position, i.e., as if the person were motioning "yes" with his head position. The positioning device 70 may further comprise support arms 84, 90 which utilize hydraulic or pneumatic devices to facilitate the placement of the patient's head. Lockable levers (now shown) allow the piston of the devices 84,90 to be operable in an unlocked position, and fixed into position in a locked position. A first end 92 of support arm 90 is rotatably connected to the mounting bracket 100, while a second end 88 is rotatably or pin connected to linkage arm 73. A first end 86 of support arm 84 is pin connected to linkage arm 73 and a second end 82 is rotatably connected via a support bracket 83 to linkage arm 77. FIGS. 8A–8F illustrates the range of motion that the positioning device 70 may operate.

Although the invention has been disclosed and described with respect to certain preferred embodiments, certain variations and modifications may occur to those skilled in the art upon reading this specification. Any such variations and modifications are within the purview of the invention notwithstanding the defining limitations of the accompanying claims and equivalents thereof.

What is claimed is:

1. Apparatus (10) for supporting the head of a patient lying on an operating table during surgery, said apparatus comprising:
   a base plate (20);
   at least three support arms (30), each of which has a first end (31) and a second end (34), said first end of each of said at least three support arms (30) being rotatably connected to said base plate (20); and
   support means (50, 60) attached to said second end (34) of each of said at least three support arms (30) for engaging and supporting the patient's head.

2. The apparatus (10) of claim 1 wherein said support means comprises a mounting pad (50) rotatably attached to said second end (34) of each of said at least three support arms (30).

3. The apparatus (10) of claim 2 wherein said second end (34) of each of said at least three support arms extends at an angle of approximately 90° from said first end (31) of each of said at least three support arms (30).

4. The apparatus (10) of claim 3 further comprising means (40) for securing each of said at least three support arms (30) in a fixed orientation.

5. The apparatus (10) of claim 1 wherein said support means comprises a skull pin (60) attached to said second end (34) of each of said at least three support arms (30).

6. The apparatus (10) of claim 5 wherein said second end (34) of each of said at least three support arms (30) extends at an angle of approximately 90° from said first end (31) of each of said at least three support arms.

7. The apparatus (10) of claim 6 further comprising means (40) for securing each of said at least three support arms (30) in a fixed orientation.

8. The apparatus (10) of claim 1 wherein said second end (34) of each of said at least three support arms (30) extends at an angle of approximately 90° from said first end (31) of each of said at least three support arms.

9. The apparatus (10) of claim 1 further comprising means (40) for securing each of said at least three support arms (30) in a fixed orientation.

10. The apparatus of claim 1 further comprising a positioning device (70) for mounting to the operating table for adjusting the height and angular position of the patient's head relative to the operating table, said base plate (20) being attached to said positioning device.

11. The apparatus of claim 10 wherein said positioning device (70) comprises:
    a mounting bracket (100) for attaching to the operating table; and
    first and second linkage arms (77, 73) pivotally connected to each other, one of said first and second linkage arms being pivotally connected to said base plate (20) and the other of said linkage arms being connected to said mounting bracket (100).

12. The apparatus of claim 11 wherein said positioning device (70) further comprises first and second telescoping arms (84, 90), said first telescoping arm being pivotally connected with each of said first and second linkage arms (77, 73), said second telescoping arm (73) being pivotally connected with one of said first and second linkage arms and with said mounting bracket (100).

13. The apparatus of claim 12 wherein at least one of said first and second telescoping arms (84, 90) comprises a piston/cylinder device.

14. The apparatus of claim 13 wherein said piston/cylinder device is pneumatic.

15. The apparatus of claim 13 wherein said piston/cylinder device is hydraulic.

* * * * *